United States Patent
LeMay et al.

(10) Patent No.: US 6,923,789 B2
(45) Date of Patent: Aug. 2, 2005

(54) MULTIPLE-COMPONENT TAMPON APPLICATOR

(75) Inventors: Jessica E. LeMay, Paramus, NJ (US); Dane R. Jackson, Bloomingdale, NJ (US); Michael L. Miller, Dover, DE (US); Wayne D. Melvin, Camden, DE (US)

(73) Assignee: Playtex Products, Inc., Westport, CT (US)

( * ) Notice: Subject to any disclaimer, the term of this patent is extended or adjusted under 35 U.S.C. 154(b) by 193 days.

(21) Appl. No.: 10/081,528

(22) Filed: Feb. 22, 2002

(65) Prior Publication Data

US 2003/0163080 A1 Aug. 28, 2003

(51) Int. Cl.[7] .................................................. A61M 5/00
(52) U.S. Cl. .................... 604/110; 604/18; 604/385.18; 604/904
(58) Field of Search ...................... 604/11–18, 385.17, 604/385.18, 904

(56) References Cited

U.S. PATENT DOCUMENTS

| | | | |
|---|---|---|---|
| 3,042,040 A | 7/1962 | Galik | 128/263 |
| 3,220,413 A | 11/1965 | Sunnen | 128/261 |
| 3,674,026 A | 7/1972 | Werner et al. | 128/263 |
| 4,048,998 A | 9/1977 | Nigro | 128/263 |
| 4,312,348 A | 1/1982 | Friese | 128/263 |
| 4,411,647 A | 10/1983 | Sakurai et al. | 604/16 |
| 4,536,178 A * | 8/1985 | Lichstein et al. | 604/15 |
| 5,041,080 A | 8/1991 | Shimatani et al. | 604/13 |
| 5,988,386 A | 11/1999 | Morrow | 206/581 |
| 6,056,714 A | 5/2000 | McNelis et al. | 604/14 |
| 6,264,626 B1 * | 7/2001 | Linares et al. | 604/15 |
| 6,524,269 B2 * | 2/2003 | McNamara | 604/12 |

* cited by examiner

*Primary Examiner*—Larry I. Schwartz
*Assistant Examiner*—Ginger Chapman
(74) *Attorney, Agent, or Firm*—Ohlandt, Greeley, Ruggiero & Perle LLP

(57) ABSTRACT

There is provided a multiple-component tampon applicator formed from at least three separate components including a barrel, a plunger, a fingergrip, an insertion tip. The at least three separate components are formed independently from one another, prior to forming the applicator. The multiple components may be formed from materials including, for example, biopolymer including starches and proteins, cardboard, heat shrink plastic, paper slurry, plastic, plastic tubing, pulp slurry, pulp-molded paper, or any combinations thereof. Methods for making a multiple component tampon applicator are also provided.

53 Claims, 7 Drawing Sheets

MULTIPLE-COMPONENT TAMPON APPLICATOR

BACKGROUND OF THE INVENTION

1. Field of the Invention

The present invention relates to an insertion device, such as a catamenial tampon applicator. More particularly, the present invention relates to a multiple-component tampon applicator formed from at least three distinct and separate components.

2. Description of the Prior Art

The majority of commercial tampon applicators are of approximately uniform cross-section and are formed from only two components, namely a barrel and a plunger. The fingergrip, if any, is formed as an integral part of the barrel component. Some applicators have a fingergrip and a plunger of a cross-sectional area reduced from that of the applicator barrel. This feature has been found not only to render the tampon applicator more grippable, but it is also more aesthetically preferred.

For current reduced cross-sectional area fingergrip tampon applicators, the tampon pledget must be loaded into the insertion end of the applicator due to the smaller opening at the fingergrip end. Thus, these tampons are restricted to top or insertion end loading. This requires the petals of the applicator, if any, to be post-formed to their final shape after the pledget has been loaded. Post-forming of petals requires the material to be plasticized. Typically, plastic petals are plasticized by heat and are easily shaped by the use of an external forming die.

On the other hand, cardboard petals are more difficult to plasticize and require the additional use of an internal mandrel. Usual methods involve heating the tip to volatize the water (either existing or supplemental moisture), and then forcing the petal into shape using an internal mandrel in conjunction with the external die. The internal mandrel has a cross-sectional area that is approximately the same as the barrel's interior, and consequently would not be able to enter through a reduced cross-sectional fingergrip area. Therefore, the necessity of the internal mandrel to shape the petal tip has thus far precluded the manufacture of a reduced cross-sectional fingergrip area on a cardboard applicator.

Therefore, there is a need for a tampon applicator, and more specifically a cardboard applicator, that can be manufactured such that petal tips can be pre-formed or integrated on the insertion end of the applicator barrel, prior to loading an absorbent pledget, using existing manufacturing processes and equipment.

SUMMARY OF THE INVENTION

It is an object of the present invention to provide a tampon applicator that is assembled from at least three distinct and separate components.

It is another object of the present invention to provide such a tampon applicator that has a barrel formed from cardboard.

It is still another object of the present invention to provide such a tampon applicator having a fingergrip with a reduced cross-sectional area compared to that of the applicator barrel.

It is a further object of the present invention to provide such a tampon applicator having petals at the insertion end of the cardboard barrel prior to loading the barrel with an absorbent pledget.

It is still a further object of the present invention to provide such a tampon applicator in which the petals are pre-formed using existing processes and equipment.

It is yet a further object of the present invention to provide such a tampon applicator in which the petals are formed on a separate and distinct insertion tip component that may be connected to a separate barrel component either before or after a pledget is loaded into the barrel component.

It is still yet a further object of the present invention to provide such a tampon applicator that prior to assembly of the applicator, and prior to loading the barrel component with an absorbent pledget, petals may be formed on the insertion end of the barrel using existing processes and equipment.

These and other objects of the present invention will be appreciated from a multiple-component tampon applicator formed from at least three separate and distinct components. A separate insertion tip component having petals may be formed. This separate component may then be connected to the barrel component either before or after an absorbent pledget is loaded into the barrel component. Also, a fingergrip may be formed as a separate component or it may be integrally formed with the barrel.

The multiple components may be formed from materials including, for example, plastic, cardboard, paper slurry, pulp slurry, pulp molded paper, heat shrink plastic, plastic tubing, biopolymers including carbohydrates and proteins, or any combinations thereof.

DETAILED DESCRIPTION OF THE INVENTION

Figure 1:
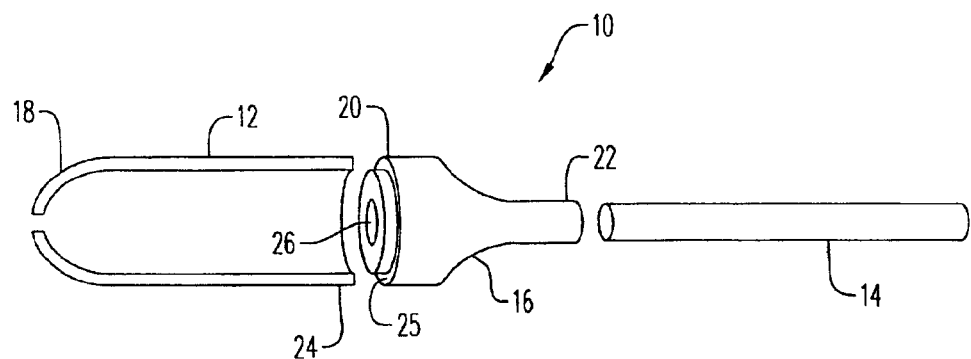
FIG. 1 is an exploded view of a multiple-component applicator having three components that form the tampon applicator of the present invention.

Referring to the drawings and in particular FIG. 1, a first embodiment of a multiple-component tampon applicator of the present invention is represented generally by reference numeral 10. One distinguishing feature of this applicator 10 is that instead of being formed from two components, namely, a barrel and a plunger, it is formed from three distinct components. In a preferred aspect of this first embodiment, the three distinct components are barrel 12, plunger 14, and fingergrip or fingergrip component 16.

The barrel 12 retains its approximately uniform cross-section, thus allowing petals 18 to be formed prior to pledget insertion. The petals 18 can be formed with the assistance of an internal mandrel, if desired.

Figure 2:
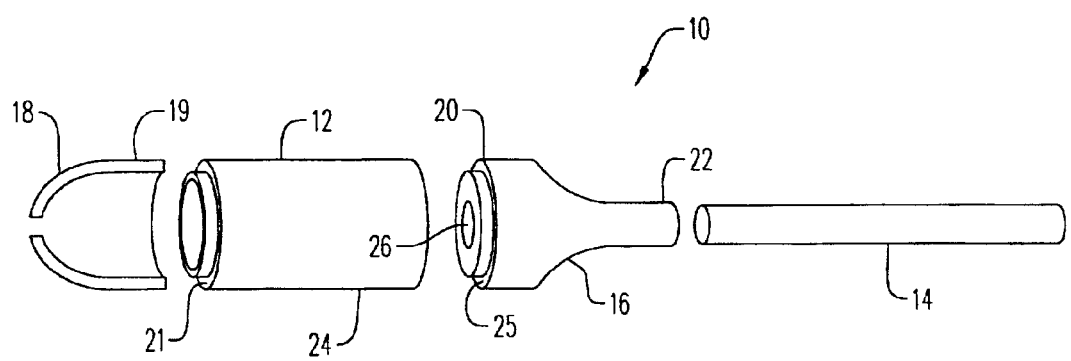
FIG. 2 is an exploded view of a multiple-component applicator having four components that form the tampon applicator of the present invention.

Referring to FIG. 2, a second embodiment of the multiple-component tampon applicator according to the present invention is depicted. This applicator 10 is formed from four distinct components. Again, as a preferred aspect of this second embodiment, the preferred components are barrel 12, plunger 14, fingergrip 16, and insertion tip 19. Petals 18 are formed on insertion tip 19. As such, an absorbent pledget may be loaded into barrel 12 either before or after insertion tip 19 is connected to barrel 12.

Figure 3:
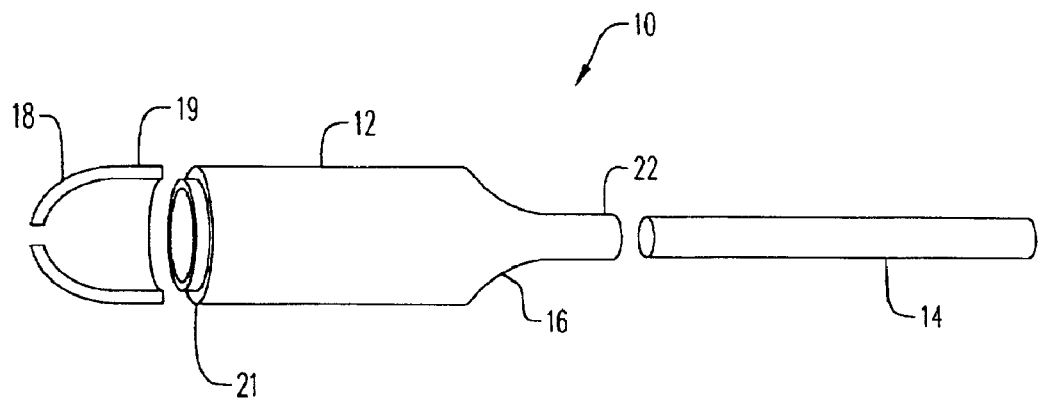
FIG. 3 is an exploded view of a three-component applicator of the present invention where the barrel component includes the fingergrip.

Referring to FIG. 3, a third embodiment of the multiple-component applicator of the present invention is shown. This applicator 10 is formed from at least three distinct components, namely, barrel 12, plunger 14, and insertion tip 19. Barrel 12 has a forward end 21. In this embodiment, fingergrip 16 is integrally formed as part of barrel 12. An absorbent pledget may be loaded into barrel 12 through forward end 21, prior to connecting insertion tip 19 to the barrel.

Barrel 12 of the multiple-component applicator 10 of the present invention may be formed from any suitable material. Suitable materials for forming barrel 12 include, for example, biopolymer, cardboard, heat shrink plastic, paper slurry, plastic, plastic tubing, pulp slurry, pulp-molded paper, or any combinations thereof. Preferably, barrel 12 is formed from cardboard. Barrel 12 may be formed from spiral wound or convolutely wound cardboard.

Any individual component that forms the multiple-component applicator, and especially barrel 12, may be internally and/or externally coated with any suitable material to enhance its strength and/or reduce surface friction. Suitable coatings include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof. It should also be understood that barrel 12, while depicted as a single component, may be formed from one or more components, such that when assembled, the one or more components form barrel 12.

Plunger 14 may be formed from any suitable material. Suitable materials for forming plunger 14 include, for example, biopolymer, cardboard, heat shrink plastic, paper slurry, plastic, plastic tubing, pulp slurry, pulp-molded paper, or any combinations thereof. Preferably, plunger 14 is formed from cardboard.

Referring to FIGS. 1 and 2, fingergrip 16, as a separate component, provides a way to create an applicator having a cardboard barrel with pre-formed petals and, perhaps, a reduced cross-sectional fingergrip area with an accompanying reduced cross-section plunger 14. Fingergrip 16 has two distinct ends, barrel or forward end 20 having a diameter approximately equal to that of barrel 12, and plunger or rearward end 22 having a diameter slightly larger than that of plunger 14. Fingergrip 16 also has channel 26, which extends axially through the entire length of the fingergrip. Channel 26 has a cross-sectional area slightly larger than that of plunger 14 so as to accommodate the plunger during assembly of applicator 10. The pledget (not shown) is loaded into barrel 12 through fingergrip or rearward end 24 of the barrel. Petals 18, if any, on barrel 12 have been pre-formed into their final shape, as in FIG. 1.

As shown in FIG. 2, when insertion tip 19 and fingergrip 16 are formed as separate components, an absorbent pledget (not shown) may be loaded either through forward end 21 or barrel rearward end 24 of barrel 12.

Referring to FIG. 3, when insertion tip 19 is formed as a distinct component, it also allows barrel 12 and fingergrip 16 to be formed as one component. With this configuration, an absorbent pledget may be loaded into barrel 12 through forward end 21, prior to assembling the multiple-component applicator.

Figure 4:
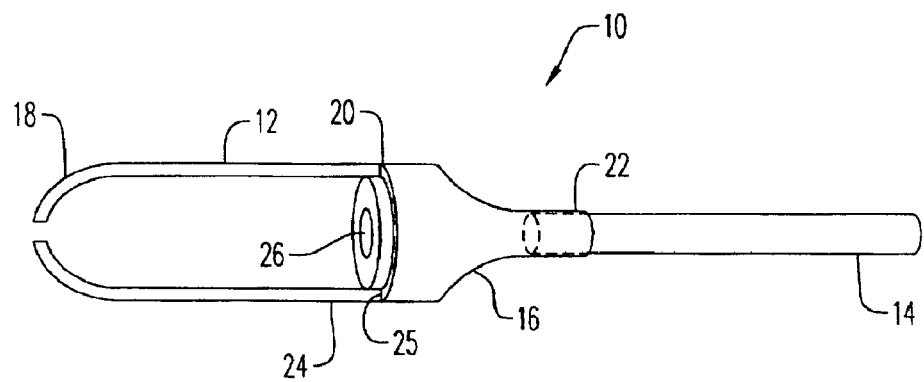
FIG. 4 is a perspective view of an assembled three-piece tampon applicator of FIG. 1.

By way of example, FIG. 4 shows the three-component applicator of FIG. 1 assembled. Once an absorbent pledget (not shown) is loaded into barrel 12, barrel forward end 20 of fingergrip 16 is connected to barrel 12 at barrel rearward end 24. Plunger 14 is then inserted into fingergrip plunger end 22 through channel 26. Alternately, plunger 14 may be loaded into channel 26 of fingergrip 16 prior to the fingergrip being connected to barrel 12. Fingergrip 16 may be secured permanently to barrel 12 by any conventional method. Preferably, fingergrip 16 is connected to barrel 12 with an adhesive. Outer edge 25 of fingergrip 16 may be of such a size that it creates a continuous surface flush with the outer edge of barrel 12.

It should be understood that the multiple-component tampon applicators depicted in FIGS. 2 and 3 may also be assembled according to the same basic tenets set forth for assembling the three-component applicator of FIG. 1. One distinguishing feature of the applicator of FIG. 2 with respect to assembly, is that the absorbent pledget may be loaded into barrel 12 either through forward end 21 or barrel rearward end 24. Therefore, the order in which the components are assembled may depend on which end of barrel 12 the pledget is loaded. A distinguishing feature of the applicator of FIG. 3, with respect to assembly, is that barrel 12 and fingergrip 16 are formed as one component, therefore, the absorbent pledget must be loaded into barrel 12 through forward end 21, prior to assembling insertion tip 19 with barrel 12.

It should also be understood that each component of the tampon applicator set forth above may be formed from one or more individual parts or sections (i.e. barrel 12, plunger 14, fingergrip 16 and/or insertion tip 19 may be formed from one or more individual parts or sections that are connected to form the component). In addition, it should be understood that while each applicator component is shown above as being discrete and separate from each other, any two or more of the components may be integrally formed and then assembled with the one or more separate components. By way of example, the insertion tip 19, the barrel 12, the fingergrip 16, and/or the plunger 14 may be integrally formed, in any combination. In addition, any component that is made up from two or more parts or sections, as set forth above, may be connected to form that component, prior to connecting with any other individual component to form an assembled applicator 10. However, the overall applicator will, nonetheless, have at least three components.

Fingergrip 16 can be formed from any suitable moldable material. Suitable moldable materials include, for example, biopolymer, cardboard, heat shrink plastic, paper slurry, plastic, plastic tubing, pulp slurry, pulp-molded paper, or any combinations thereof. In a preferred embodiment of the present invention, fingergrip 16 is formed from pulp molded paper.

Figure 5:
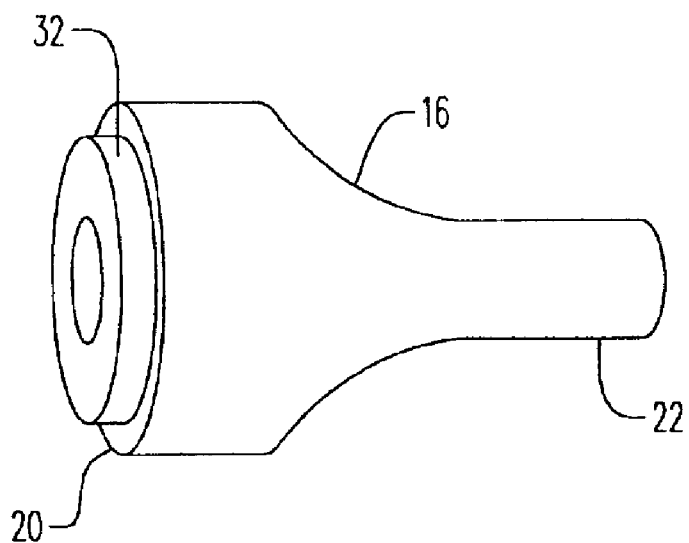
FIG. 5 is a perspective view of a fingergrip component of the tampon applicator of FIG. 1.

FIG. 5 is another embodiment of the present invention. Fingergrip 16 is formed with a connector ring 32 on barrel forward end 20. Connector ring 32 has a diameter slightly larger than the internal diameter of barrel 12 so that fingergrip 16 can be connected and secured to barrel 12 by interference fit.

Figure 6:
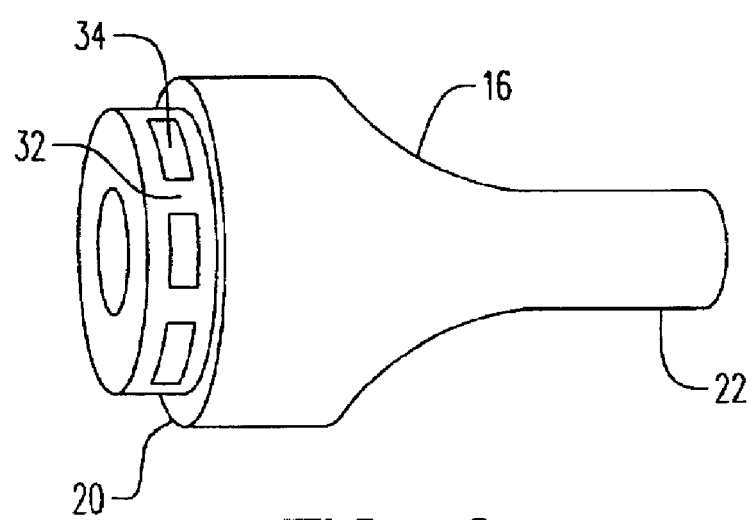
FIG. 6 is a perspective view of a fingergrip component according to another embodiment of the present invention.

FIG. 6 is another embodiment of the present invention. Connector ring 32 may be formed with one or more tabs, ridges and/or slots 34. One or more tabs, ridges and/or slots 34 can interlock with corresponding tabs, ridges and/or slots (not shown) formed on the inner surface of barrel 12, thus securing fingergrip 16 to barrel 12. The one or more tabs, ridges and or slots may be formed on external and/or internal surfaces.

Figure 7:
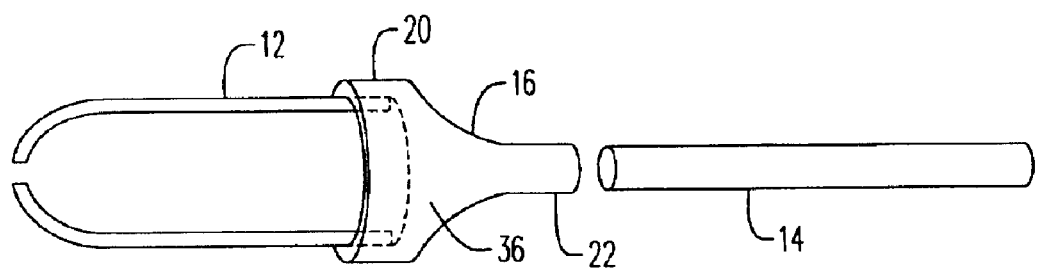
FIG. 7 is a perspective view of a three-piece applicator according to yet another embodiment of the present invention.
Figure 8A:
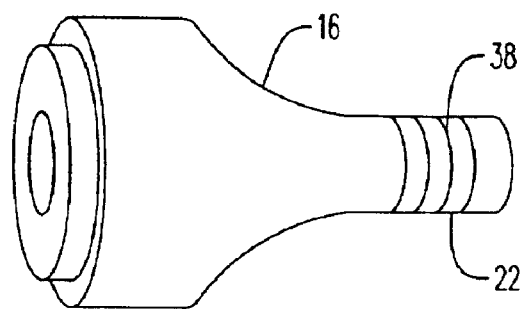
FIG. 8 is a perspective view of several embodiments of fingergrip components having various gripping structures according to the present invention.
Figure 8B:
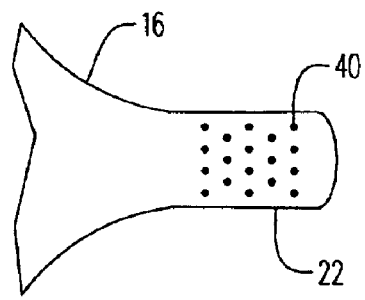
Figure 8C:
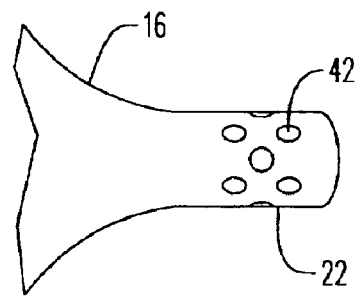
Figure 8D:
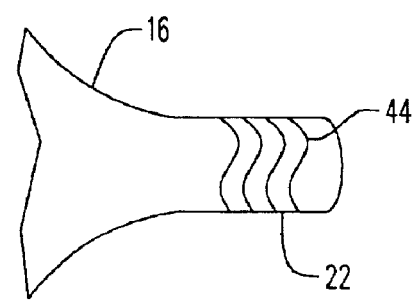

FIG. 7 is another embodiment of the present invention. In this embodiment, fingergrip 16 is formed from a heat-shrinkable material 36 that has an initial diameter larger than the outer diameter of barrel 12, and shrinks to a diameter at least as small as plunger 14. Heat-shrinkable material 36 at barrel end 20 is shrunk to fit the outside of barrel 12 snugly. The union between heat-shrinkable material 36 and barrel 12 can be reinforced with an adhesive. Plunger or rearward end 22 of fingergrip 16 is shrunk so that it is just larger than the outside diameter of plunger 14.

The fingergrip 16 may be formed with any number and/or configuration of gripping structures, to further enhance the applicator's grippability. Fingergrip 16 may be smooth or, more preferably, may include one or more patterned or textured structures extending above and/or below the surface of the fingergrip.

The gripping structures may include, for example, one or more abrasive materials, embossments, grooves, high wet coefficient of friction materials, lances, pressure sensitive adhesives, protuberances, slits, treads, or any combinations thereof. In addition, the gripping structures may be formed in any shape, including, for example, arc, circle, concave, cone, convex, diamond, line, oval, polygon, rectangle, rib, square, triangle, or any combinations thereof.

Referring to FIG. 8, by way of example, several different fingergrip embodiments having various gripping structures are depicted. FIG. 8A depicts fingergrip 16 with one or more bands 38 circumferentially disposed around fingergrip rearward end 22. FIG. 8B depicts fingergrip 16 with one or more dot-like structures 40 disposed circumferentially around fingergrip rearward end 22. FIG. 8C depicts fingergrip 16 with one or more circular structures 42 disposed circumferentially around fingergrip rearward end 22. FIG. 8D depicts fingergrip 16 with two or more wavy bands 44 disposed circumferentially around fingergrip rearward end 22.

It should be understood that the gripping structures may be arranged circumferentially around fingergrip 16 in any pattern suitable for forming a gripping area. For example, the gripping structures can form a distinct pattern, such as, rows, columns or may be formed intermittently with breaks in structure or in any random order or pattern.

Figure 9:
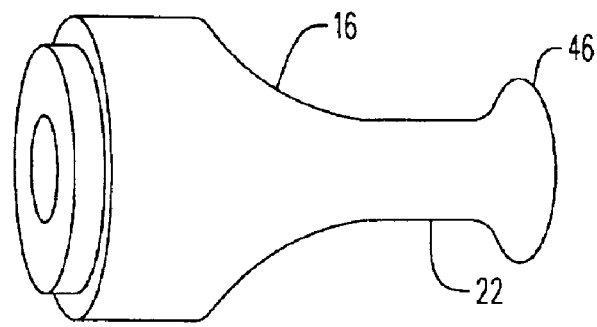
FIG. 9 is a perspective view of a fingergrip component according to another embodiment of the present invention.

FIG. 9 is another embodiment of the present invention. In this embodiment, fingergrip rearward end 22 may be formed with a circumferentially flared or ridge-like structure end 46, to further enhance the gripping characteristics of the applicator.

Figure 10:
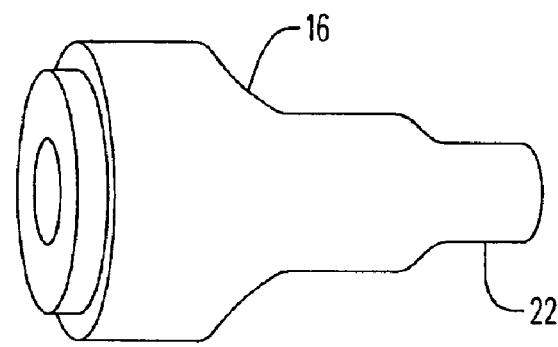
FIG. 10 is a perspective view of a fingergrip component according to another embodiment of the present invention.

FIG. 10 is another embodiment of the present invention. In this embodiment, fingergrip rearward end 22 is formed with a stepped taper to further enhance the gripping characteristics of the applicator.

Figure 11:
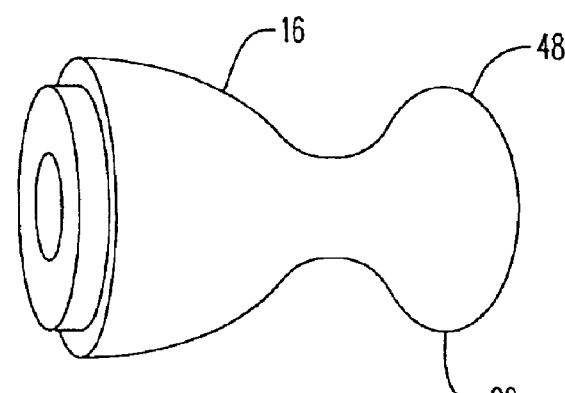
FIG. 11 is a perspective view of a fingergrip component according to another embodiment of the present invention.

FIG. 11 is another embodiment of the present invention. In this embodiment, fingergrip rearward end 22 may be formed with a knob-like structure 48 to further enhance the gripping characteristics of the applicator.

Any combinations of the features depicted in FIGS. 8 through 11, and described above, are possible as well. In addition, the gripping structures could be raised, depressed, or any combination thereof, with respect to the surface of the fingergrip area. The gripping structures can be formed in any shape, in any number, and in any pattern or configuration suitable for forming an enhanced gripping area on fingergrip 16. As such, it should be clear that the present invention is in no way limited by those features depicted or described above.

It is also understood that the cross-section of barrel 12, plunger 14, fingergrip 16 and insertion tip 19 can be circular, oval, polygonal or elliptical. Also, insertion tip 19 can be tapered, elliptical, dome-shaped or flat. Barrel 12 can be straight, tapered, or curvilinear along its length.

Figure 12:
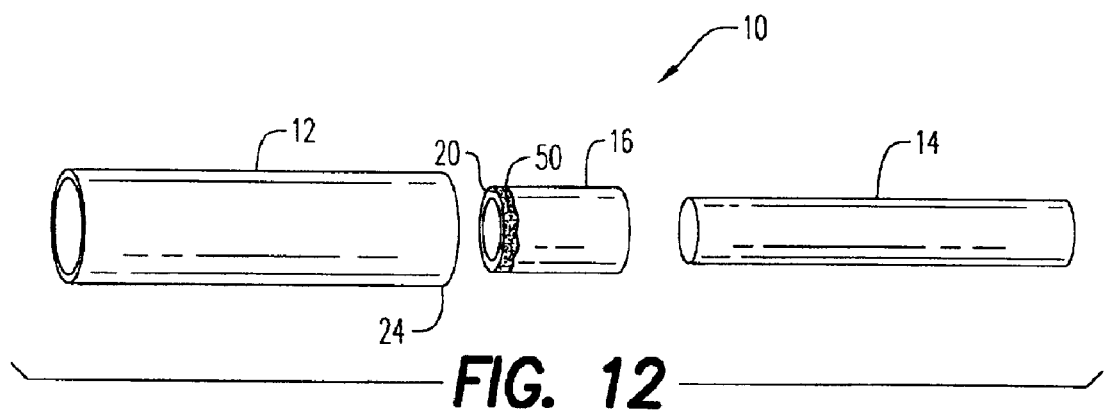
FIG. 12 is a perspective view of a multiple-component applicator having three components that form one embodiment of a tampon applicator of the present invention.
Figure 13:
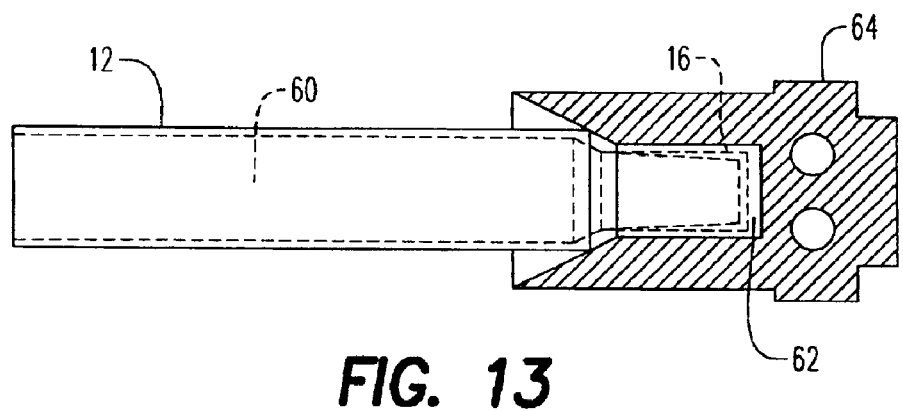
FIG. 13 is a perspective view of the fingergrip and barrel components of FIG. 12 in a heated former.
Figure 14:
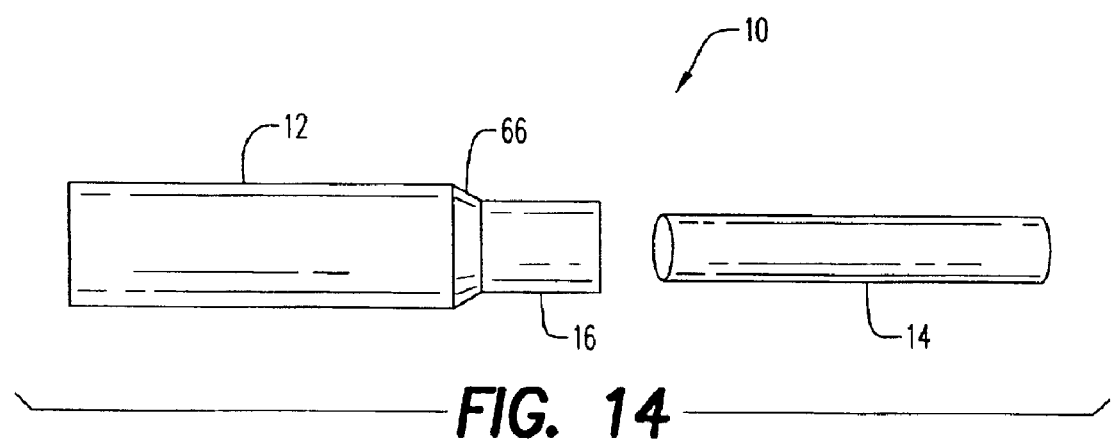
FIG. 14 is a perspective view of a multiple-component applicator with the barrel and fingergrip formed in the heated former of FIG. 13.

Referring to FIGS. 12 through 14, a method of assembling a multiple component tampon according to another embodiment of the present invention is depicted. Applicator 10 has independent or discrete barrel 12, plunger 14 and fingergrip 16. To assemble the components, adhesive 50 is applied to the fingergrip barrel end 20. As depicted in FIG. 13, fingergrip 16 is inserted into cavity 62 of heated shaper 64. Mandrel 60 is inserted into fingergrip 16 housed in cavity 62. Barrel 12 is inserted over mandrel 60. The barrel 12 and fingergrip 16 are allowed to remain in position in heated shaper 64 for about 1 to 20 seconds and more preferably 5 to 10 seconds.

Referring to FIG. 14, when removed from the mandrel 60 and heated shaper 64, the fingergrip 16 is connected to barrel 12 at tapered rearward end 66. Plunger 14 may then be inserted into fingergrip 16.

The foregoing specification and drawings are merely illustrative of the present invention and are not intended to limit the invention to the disclosed embodiments. Variations and changes, which are obvious to one skilled in the art are intended to be within the scope and nature of the present invention, which is defined in the appended claims.

What is claimed is:

1. A multiple-component tampon applicator formed from at least three separate components selected from the group consisting of a barrel, a fingergrip, a plunger, and an insertion tip,
    wherein said at least three separate components are formed independently from one another, prior to forming said applicator, and
    wherein at least one of said at least three separate components is said fingergrip, and wherein said fingergrip further comprises at least one gripping structure and said at least one gripping structure is raised, depressed, or a combination thereof.

2. The applicator of claim 1, wherein one or more of said at least three separate components are formed from a material selected from the group consisting of biopolymer, cardboard, heat shrink plastic, paper slurry, plastic, plastic tubing, pulp slurry, pulp-molded paper, and any combinations thereof.

3. The applicator of claim 1, wherein two or more of said at least three separate components are formed from a material selected from the group consisting of biopolymer, cardboard, heat shrink plastic, paper slurry, plastic, plastic tubing, pulp slurry, pulp-molded paper, and any combinations thereof.

4. The applicator of claim 1, wherein three or more of said at least three separate components are formed from a material selected from the group consisting of biopolymer, cardboard, heat shrink plastic, paper slurry, plastic, plastic tubing, pulp slurry, pulp-molded paper, and any combinations thereof.

5. The applicator of claim 1, wherein at least one of said at least three separate components are coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

6. The applicator of claim 1, wherein at least one of said at least three separate components is said barrel, and wherein said barrel is formed from cardboard.

7. The applicator of claim 1, wherein said barrel has a forward end and a rearward end opposite said forward end.

8. The applicator of claim 7, wherein said barrel further comprises three to eight petals disposed on said forward end.

9. The applicator of claim 1, wherein said fingergrip is formed from pulp molded paper.

10. The applicator of claim 1, wherein said fingergrip has a forward end, a rearward end, and an axially extending channel.

11. The applicator of claim 10, wherein said fingergrip has a reduced cross-sectional area from that of said barrel, and wherein a cross-sectional area of said fingergrip at said forward end is larger than a cross-sectional area at said rearward end of said fingergrip.

12. The applicator of claim 10, wherein said channel has a cross-sectional area adapted to accommodate said plunger.

13. The applicator of claim 1, wherein said at least one gripping structure is circumferentially disposed around said fingergrip.

14. The applicator of claim 1, wherein said at least one gripping structure is selected from the group consisting of one or more abrasive materials, embossments, grooves, high wet coefficient of friction materials, lances, pressure sensitive adhesives, protuberances, slits, treads, and any combinations thereof.

15. The applicator of claim 1, wherein said at least one gripping structure is formed in a shape selected from the group consisting of arc, circle, concave, cone, convex, diamond, line, oval, polygon, rectangle, rib, square, triangle, and any combinations thereof.

16. An applicator having three separate components, the three separate components comprising:
    a barrel having petals pre-formed on an insertion end of said barrel prior to loading said barrel with an absorbent pledget;
    a fingergrip having a reduced cross-sectional area; and
    a plunger having a reduced cross-sectional area;
    wherein said barrel, fingergrip and plunger are formed as the three separate components, prior to forming the applicator.

17. The applicator of claim 16, wherein one or more of said three separate components are individually formed from a material selected from the group consisting of biopolymer, cardboard, heat shrink plastic, paper slurry, plastic, plastic tubing, pulp slurry, pulp-molded paper, and any combinations thereof.

18. The applicator of claim 16, wherein two or more of said three separate components are individually formed from a material selected from the group consisting of biopolymer, cardboard, heat shrink plastic, paper slurry, plastic, plastic tubing, pulp slurry, pulp-molded paper, and any combinations thereof.

19. The applicator of claim 16, wherein at least one of said three separate components is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

20. The applicator of claim 16, wherein said barrel is formed from cardboard.

21. The applicator of claim 16, wherein said fingergrip has a forward end, a rearward end, and an axially extending channel.

22. The applicator of claim 21, wherein said reduced cross-sectional area of said fingergrip at said forward end is larger than a cross-sectional area at said rearward end of said fingergrip.

23. The applicator of claim 21, wherein said channel has a cross-sectional area adapted to accommodate said plunger.

24. The applicator of claim 16, wherein said fingergrip further comprises at least one gripping structure.

25. The applicator of claim 24, wherein said at least one gripping structure is circumferentially disposed around said fingergrip.

26. The applicator of claim 24, wherein said at least one gripping structure is selected from the group consisting of one or more abrasive materials, embossments, grooves, high wet coefficient of friction materials, lances, pressure sensitive adhesives, protuberances, slits, treads, and any combinations thereof.

27. The applicator of claim 24, wherein said at least one gripping structure is formed in a shape selected from the group consisting of arc, circle, concave, cone, convex, diamond, line, oval, polygon, rectangle, rib, square, triangle, and any combinations thereof.

28. The applicator of claim 24, wherein said at least one gripping structure is raised, depressed, or a combination thereof.

29. A method of making an applicator having three separate components comprising the steps of:
    (a) forming a barrel having a forward end and a rearward end;
    (b) forming a fingergrip having a forward end, a rearward end, and an axially extending channel between said forward end and said rearward end;
    (c) forming a plunger having a forward end and a rearward end; and
    (d) connecting said forward end of said fingergrip with said rearward end of said barrel.

30. The method of claim 29, further comprising, following step (d), a step of inserting said forward end of said plunger into said channel of said rearward end of said fingergrip.

31. The method of claim 29, further comprising, prior to step (d), a step of inserting said rearward end of said plunger into said channel of said forward end of said fingergrip.

32. The method of claim 29, further comprising, prior to step (a), a step of pre-forming three to eight petals on said forward end of said barrel.

33. The method of claim 29, wherein one or more of said three separate components are formed from a material selected from the group consisting of biopolymer, cardboard, heat shrink plastic, paper slurry, plastic, plastic tubing, pulp slurry, pulp-molded paper, and any combinations thereof.

34. The method of claim 29, wherein two or more of said three separate components are formed from a material selected from the group consisting of biopolymer, cardboard, heat shrink plastic, paper slurry, plastic, plastic tubing, pulp slurry, pulp-molded paper, and any combinations thereof.

35. The method of claim 29, wherein at least one of said three separate components is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

36. The method of claim 29, wherein said forward end of said fingergrip has an external cross-sectional area slightly larger than an internal cross-sectional area of said rearward end of said barrel, and wherein said fingergrip and said barrel are connectably secured by interference fit.

37. The method of claim 29, wherein said forward end of said fingergrip has an internal cross-sectional area slightly smaller than an external cross-sectional area of said rearward end of said barrel, and wherein said fingergrip and said barrel are connectably secured by interference fit.

38. The method of claim 29, wherein said forward end of said fingergrip further comprises one or more internal tabs, ridges, slots, and any combination thereof, for securably connecting said fingergrip to said barrel.

39. The method of claim 29, wherein said forward end of said fingergrip further comprises one or more external tabs, ridges, slots, and any combination thereof, for securably connecting said fingergrip to said barrel.

40. The method of claim 29, wherein said rearward end of said barrel further comprises one or more internal tabs, ridges, slots, and any combination thereof, for securably connecting said barrel to said fingergrip.

41. The method of claim 29, wherein said rearward end of said barrel further comprises one or more external tabs, ridges, slots, and any combination thereof, for securably connecting said barrel to said fingergrip.

42. The method of claim 29, wherein said fingergrip is formed from heat-shrinkable material having a diameter larger than a diameter of said barrel, and wherein said heat-shrinkable material is shrunk to securably fit over an outside surface of said barrel.

43. The method of claim 42, wherein said heat-shrinkable material is further shrunk at said rearward end of said fingergrip to form a reduced cross-sectional area.

44. A method of making an applicator comprising the steps of:

(a) forming a barrel having an forward end and a rearward end;

(b) forming a fingergrip having a forward end, a rearward end, and an axially extending channel between said forward end and said rearward end; and (c) inserting said fingergrip and said barrel into a heat former, wherein said barrel and said fingergrip are fused into a unitary fingergrip barrel portion.

45. The method of claim 44, further comprising, after step (b), a step of applying adhesive to said forward end of said fingergrip.

46. The method of claim 44, further comprising, after step (b), a step of applying adhesive to said rearward end of said barrel.

47. The method of claim 44, wherein said fingergrip and said barrel are formed from a material selected from the group consisting of biopolymer, cardboard, heat shrink plastic, paper slurry, plastic, plastic tubing, pulp slurry, pulp-molded paper, and any combinations thereof.

48. The method of claim 44, wherein at least one of said barrel and fingergrip is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

49. The applicator of claim 44, wherein said fingergrip further comprises at least one gripping structure.

50. The applicator of claim 49, wherein said at least one gripping structure is circumferentially disposed around said fingergrip.

51. The applicator of claim 49, wherein said at least one gripping structure is selected from the group consisting of one or more abrasive materials, embossments, grooves, high wet coefficient of friction materials, lances, pressure sensitive adhesives, protuberances, slits, treads, and any combinations thereof.

52. The applicator of claim 49, wherein said at least one gripping structure is formed in a shape selected from the group consisting of arc, circle, concave, cone, convex, diamond, line, oval, polygon, rectangle, rib, square, triangle, and any combinations thereof.

53. The applicator of claim 49, wherein said at least one gripping structure is raised above, depressed below, or a combination thereof, a surface of said barrel.

* * * * *

(12) INTER PARTES REEXAMINATION CERTIFICATE (609th)
United States Patent
LeMay et al.

(10) Number: US 6,923,789 C1
(45) Certificate Issued: Jun. 3, 2013

(54) MULTIPLE-COMPONENT TAMPON APPLICATOR

(75) Inventors: Jessica E. LeMay, Paramus, NJ (US); Dane R. Jackson, Bloomingdale, NJ (US); Michael L. Miller, Dover, DE (US); Wayne D. Melvin, Camden, DE (US)

(73) Assignee: Wells Fargo Bank, National Association, Middletown, CT (US)

Reexamination Request:
No. 95/001,415, Aug. 5, 2010

Reexamination Certificate for:
Patent No.: 6,923,789
Issued: Aug. 2, 2005
Appl. No.: 10/081,528
Filed: Feb. 22, 2002

(51) Int. Cl.
*A61M 5/00* (2006.01)

(52) U.S. Cl.
USPC ......... 604/110; 604/385.18; 604/904; 604/18

(58) Field of Classification Search
None
See application file for complete search history.

(56) References Cited

To view the complete listing of prior art documents cited during the proceeding for Reexamination Control Number 95/001,415, please refer to the USPTO's public Patent Application Information Retrieval (PAIR) system under the Display References tab.

*Primary Examiner* — Beverly M. Flanagan

(57) ABSTRACT

There is provided a multiple-component tampon applicator formed from at least three separate components including a barrel, a plunger, a fingergrip, an insertion tip. The at least three separate components are formed independently from one another, prior to forming the applicator. The multiple components may be formed from materials including, for example, biopolymer including starches and proteins, cardboard, heat shrink plastic, paper slurry, plastic, plastic tubing, pulp slurry, pulp-molded paper, or any combinations thereof. Methods for making a multiple component tampon applicator are also provided.

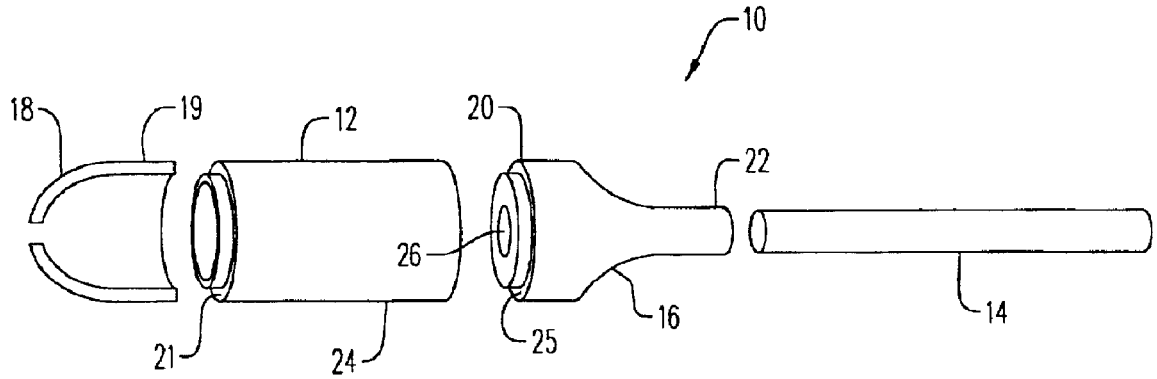

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-53 are cancelled.

* * * * *